United States Patent [19]

Carey et al.

[11] Patent Number: 4,481,199

[45] Date of Patent: Nov. 6, 1984

[54] 1,2,4-TRIAZOLE-3-AMINE AND 1,2,4 TRIAZOLE-3,5-DIAMINE COMPOUNDS AND THEIR PHARMACEUTICAL USE

[75] Inventors: Linda Carey; Barry J. Price; John W. Clitherow; John Bradshaw; Michael Martin-Smith; David E. Bays; Philip Blatcher, all of Hertfordshire, England

[73] Assignee: Glaxo Group Limited, England

[21] Appl. No.: 511,234

[22] Filed: Jul. 6, 1983

Related U.S. Application Data

[63] Continuation of Ser. No. 296,841, Aug. 27, 1981, abandoned.

[30] Foreign Application Priority Data

Aug. 27, 1980 [GB] United Kingdom ............... 8027741

[51] Int. Cl.$^3$ .................. A61K 31/41; C07D 405/12; C07D 405/14
[52] U.S. Cl. .............................. 424/246; 424/248.51; 424/248.56; 424/251; 424/263; 424/267; 424/269; 424/272; 424/270; 544/60; 544/124; 544/134; 544/180; 544/215; 544/333

[58] Field of Search ............... 548/266, 267, 268, 161, 548/212, 233, 245, 246; 546/193, 194, 210, 276; 544/60, 124, 134, 215, 180, 333; 424/246, 248.51, 248.56, 248.54, 251, 263, 267, 269, 270, 272

[56] References Cited

U.S. PATENT DOCUMENTS 4,318,913 3/1982 Clitherow et al. .................. 546/210
4,323,566 4/1982 Clitherow et al. ............. 424/248.51

FOREIGN PATENT DOCUMENTS 2003471A 3/1979 United Kingdom ............... 424/263
2023133 12/1979 United Kingdom ............... 548/266

Primary Examiner—Robert T. Bond
Attorney, Agent, or Firm—Bacon & Thomas

[57] ABSTRACT

The invention provides compounds of the general formula (I)

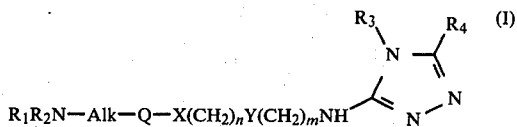

and physiologically acceptable salts, hydrates and bioprecursors thereof, in which the substituents are defined later.

The compounds show pharmacological activity as selective histamine $H_2$-antagonists.

11 Claims, No Drawings

1,2,4-TRIAZOLE-3-AMINE AND 1,2,4 TRIAZOLE-3,5-DIAMINE COMPOUNDS AND THEIR PHARMACEUTICAL USE

This application is a continuation of application Ser. No. 296,841, filed Aug. 27, 1981 now abandoned.

This invention relates to novel heterocyclic derivatives having action on histamine receptors, to processes for the preparation thereof, to pharmaceutical compositions containing them and to their use in therapeutics.

Certain novel heterocyclic derivatives have now been found which have potent activity as $H_2$-antagonists. These compounds, which are more particularly described below, for example show inhibition of the secretion of gastric acid when this is stimulated via histamine receptors (Ash and Schild, Brit. J. Pharmacol. Chemother, 1966, 27, 427). Their ability to do so can be demonstrated in the perfused rat stomach using the method described in German Offenlegungsschrift No. 2,734,070, modified by the use of sodium pentobarbitone (50 mg/kg) as anaesthetic instead of urethane, and in conscious dogs equipped with Heidenhain pouches using the method described by Black et al, Nature 1972 236, 385. Furthermore the compounds antagonise the effect of histamine on the contraction frequency of isolated guinea pig right atrium but do not modify histamine induced contractions of isolated gastrointestinal smooth muscle which are mediated via $H_1$-receptors.

Compounds with histamine $H_2$-blocking activity may be used in the treatment of conditions where there is an advantage in lowering gastric acidity, particularly in gastric and peptic ulceration, as a prophylactic measure in surgical procedures, and in the treatment of allergic and inflammatory conditions where histamine is a known mediator. Thus they may be used for example, either alone or in combination with other active ingredients in the treatment of allergic and inflammatory conditions of the skin.

The present invention provides compounds of the general formula (I)

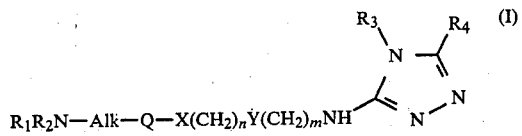

and physiologically acceptable salts, hydrates and bioprecursors thereof, in which $R_1$ represents $C_{1-14}$ alkyl, cycloalkyl, alkenyl, alkynyl, aralkyl, trifluoroalkyl, heteroaralkyl or alkyl substituted by cycloalkyl, hydroxy, alkoxy, amino, alkylamino or dialkylamino; and $R_2$ represents hydrogen or a $C_{1-4}$ alkyl group;

or $R_1$ and $R_2$ together with the nitrogen atom to which they are attached form a 5–10 membered ring which may be saturated or may contain at least one double bond, may be unsubstituted or may be substituted by one or more $C_{1-3}$ alkyl groups, e.g. methyl, or a hydroxy group and/or may contain another heteroatom selected from oxygen and sulphur;

Alk represents a straight or branched alkylene chain of 1 to 6 carbon atoms;

Q represents a furan or thiophen ring in which incorporation into the rest of the molecule is through bonds at the 2- and 5- positions, the furan or thiophen ring optionally bearing a further substituent $R_5$ adjacent to the group $R_1R_2N$-Alk, or Q represents a benzene ring in which incorporation into the rest of the molecule is through bonds at the 1- and 3- or 1- and 4- positions;

$R_5$ represents halogen or $C_{1-4}$ alkyl which may be substituted by hydroxy or $C_{1-4}$ alkoxy;

X and Y, which may be the same or different each represent oxygen, sulphur, methylene or a bond;

n represents zero, 1, 2 or 3 and m represents an integer from 2 to 5 with the provisos that (a) the total number of atoms in the chain $X(CH_2)_nY(CH_2)_m$ is an integer from 3 to 8 and (b) when X and Y represent oxygen or sulphur then n is 2 or 3;

$R_3$ represents alkyl, alkenyl, aralkyl, hydroxy-$C_{2-6}$ alkyl or alkoxy-$C_{2-6}$ alkyl; and $R_4$ represents hydrogen, alkyl, alkenyl, aralkyl, acyloxyalkyl, alkylthioalkyl, arylthioalkyl, aryloxyalkyl, aralkyloxyalkyl, or the group $(CH_2)_qR_6$ where q is zero, 1,2,3,4,5 or 6 and the alkylene chain $(CH_2)_q$ may be straight or branched, and $R_6$ is hydroxy, alkoxy, nitro, cyano, heteroaryl or $CH_2NHC(=A)NHR_7$ where A is NCN, $NSO_2$Methyl, $NSO_2$Phenyl or $CHNO_2$, and $R_7$ is alkyl;

or $R_6$ is the group $NR_8R_9$ where $R_8$ is hydrogen or alkyl; and $R_9$ is hydrogen, alkyl, alkenyl, aryl, aralkyl or heteroaralkyl, or $R_9$ is the group $SO_2R_{10}$ where $R_{10}$ is alkyl or aryl; or $R_9$ is the group $COR_{11}$ where $R_{11}$ is hydrogen, alkyl, aryl, aralkyl, alkoxy, halomethyl, heteroaryl, heteroaralkyl or the group $NHR_{12}$ where $R_{12}$ is hydrogen, alkyl, cycloalkyl, aryl or aralkyl; or $R_8$ and $R_9$ together represent the group $=CR_{13}R_{14}$ where $R_{13}$ represents aryl or heteroaryl and $R_{14}$ represents hydrogen or alkyl;

or $R_6$ is the group $SO_2R_{15}$ in which $R_{15}$ is hydroxy, alkyl, aryl or the group $NR_{16}R_{17}$ where $R_{16}$ and $R_{17}$, which may be the same or different, each represent hydrogen or alkyl;

or $R_6$ is the group $COR_{18}$ where $R_{18}$ is hydrogen, hydroxy, alkoxy, aryloxy, aralkyloxy, alkyl, aryl, aralkyl or the group $NR_{19}R_{20}$ where $R_{19}$ is hydrogen or alkyl optionally substituted by a hydroxy or alkoxy group; and $R_{20}$ is hydrogen, alkyl (optionally substituted by a hydroxy or alkoxy group), alkenyl, aryl, aralkyl or cycloalkyl, or $NR_{19}R_{20}$ forms a 5 to 8 membered ring which may contain another heteroatom, e.g. oxygen, or a double bond and/or may be substituted by hydroxy or one or two $C_{1-3}$ alkyl (e.g. methyl) groups; or $R_6$ is the group $CR_{21}=NR_{22}$ where $R_{21}$ is hydrogen, alkyl, aryl or aralkyl and $R_{22}$ is hydroxy, alkoxy, aralkyloxy or $-NHC(=B)NH_2$ where B is oxygen or sulphur;

with the proviso that when the group $R_6$ contains a carbon atom through which it is linked to the alkylene group $(CH_2)_q$ then the total number of carbon atoms in the resulting chain is not greater than 6 (i.e. q is not greater than 5);

or $R_3$ and $R_4$ together represent the group $-(CH=CH)_2$ or $-(CH_2)_4-$.

The term "alkyl" as a group or part of a group means that the group is straight or branched, and unless otherwise stated, has preferably 1 to 6 carbon atoms and in particular 1 to 4 carbon atoms, e.g. methyl or ethyl, and the terms "alkenyl" and "alkynyl" mean that the groups preferably contain 3–6 carbon atoms. The term "cycloalkyl" means that the group has 3 to 8 carbon atoms. The term "halomethyl" means a mono-, di- or trihalo substituted methyl group, e.g. trifluoromethyl. The term "aryl" as a group or part of a group preferably means phenyl or substituted phenyl, for example phenyl substituted with one or more $C_{1-3}$ alkyl or alkoxy groups or halogen atoms, e.g. fluorine. The acyl portion of an acyloxyalkyl group means an aroyl, aralkanoyl or $C_{1-6}$ alkanoyl group. Examples of acyloxyalkyl groups include acetoxymethyl, formyloxymethyl, benzoyloxymethyl and phenylacetoxymethyl. The term "heteroaryl" as a group or part of a group means a 5 or 6 membered monocyclic ring containing 1 to 3 heteroatoms selected from oxygen, nitrogen and sulphur, e.g. thienyl, pyridyl, furyl or thiazolyl. The heteroaryl ring may be unsubstituted or substituted by $C_{1-3}$ alkyl, $C_{1-3}$ alkoxy, hydroxy, hydroxyalkyl, aminoalkyl, alkylaminoalkyl, dialkylaminoalkyl or halogen. The alkyl portion of a heteroaralkyl group is a straight or branched $C_{1-4}$ alkyl chain, and the heteroaryl ring is linked to the alkyl portion through either a carbon or nitrogen atom.

According to one aspect the invention provides compounds of formula (I) in which $R_4$ represents hydrogen, alkyl, alkenyl, aralkyl, acyloxyalkyl, aryloxyalkyl, aralkyloxyalkyl, or the group $(CH_2)qR_6$ where $R_6$ represents hydroxy or alkoxy, or $R_6$ is $NR_8R_9$ where $R_9$ represents hydrogen or alkyl;

or, when q is zero, $R_6$ represents $NR_8R_9$ where $R_9$ is alkenyl, aralkyl or heteroaralkyl, or $R_9$ is the group $SO_2R_{10}$ or the group $COR_{11}$ (where $R_{11}$ is other than halomethyl); or $R_8$ and $R_9$ together represent $=CR_{13}R_{14}$.

According to another aspect the invention provides compounds of formula (I) in which $R_4$ represents alkylthioalkyl or arylthioalkyl, or the group $(CH_2)qR_6$ where $R_6$ is nitro, cyano, heteroaryl, or $CH_2NHC(=A)NHR_7$; or $R_6$ represents $CH_2NR_8R_9$ where $R_9$ is aryl, aralkyl, alkenyl, or heteroaralkyl, or $R_9$ is the group $SO_2R_{10}$ or $COR_{11}$, or $R_8$ and $R_9$ together represent $=CR_{13}R_{14}$; or $R_6$ represents $SO_2R_{15}$, $COR_{18}$ or $CR_{2]}=NR_{22}$;

or $R_3$ and $R_4$ together represent $-(CH=CH)_2$ or $-(CH_2)_4-$

Examples of suitable meanings for the groups $R_1$ to $R_4$ are as follows:

$R_1$: alkyl containing up to 14 carbon atoms (e.g. methyl, ethyl, propyl, butyl, pentyl, hexyl, heptyl or decyl), $C_{5-7}$ cycloalkyl (e.g. cyclopentyl, cyclohexyl or cycloheptyl), alkenyl, (e.g. allyl or 3,3-dimethylallyl), aralkyl (e.g. phenylalkyl such as benzyl or phenethyl), $C_{1-4}$ alkyl substituted by a trifluoromethyl group (e.g. 2,2,2-trifluoroethyl), hydroxy $C_{2-4}$ alkyl (e.g. 3-hydroxypropyl), $C_{1-3}$ alkoxy $C_{2-4}$ alkyl (e.g. methoxyethyl or ethoxyethyl), or di-$C_{1-3}$ alkylamino $C_{2-4}$ alkyl (e.g. dimethylaminoethyl, diethylaminoethyl or dimethylaminopropyl), or heteroaralkyl where the heterocyclic portion represents for example a furyl, thienyl, pyrrolyl, pyridinyl, pyrimidinyl, triazinyl, oxazolyl, triazolyl or thiazolyl ring and the alkyl portion is for example a methyl, ethyl or propyl grouping;

$R_2$: hydrogen, methyl or ethyl; or $R_1R_2N$ may represent a 5-8 membered ring optionally containing one double bond and/or substituted by one or two $C_{1-3}$ alkyl (e.g. methyl) groups or a hydroxy group and/or containing an oxygen or sulphur atom (e.g. pyrrolidino, piperidino, hexamethylenimino, heptamethylenimino, tetrahydropyridino, 4-hydroxypiperidino, 4-$C_{1-3}$ alkylpiperidino (e.g. 4-methylpiperidino), morpholino, 2,6-di-$C_{1-3}$ alkylmorpholino (e.g. 2,6-dimethylmorpholino), or thiamorpholino;

$R_3$: $C_{1-4}$ alkyl (e.g. methyl, ethyl or propyl) or hydroxy $C_{2-4}$ alkyl) (e.g. 2-hydroxyethyl);

$R_4$: hydrogen, hydroxy, $C_{1-4}$ alkyl (e.g. methyl, ethyl, or isobutyl), hydroxy $C_{1-4}$ alkyl (e.g. hydroxymethyl, 2-hydroxyethyl or 1-hydroxy-1-methylethyl), $C_{1-3}$ alkoxy $C_{1-4}$ alkyl (e.g. methoxymethyl or methoxyethyl), phenyl $C_{1-3}$ alkyl (e.g. benzyl or phenethyl), $C_{2-4}$ alkanoyloxy $C_{1-4}$ alkyl (e.g. acetoxymethyl), amino $C_{1-4}$ alkyl (e.g. aminomethyl), $C_{1-3}$alkylthio $C_{1-4}$ alkyl (e.g. methylthiomethyl), amino, $C_{1-4}$ alkylamino (e.g. methylamino or ethylamino) or di-$C_{1-4}$ alkylamino (e.g. dimethylamino, diethylamino or dipropylamino), phenyl $C_{1-3}$ alkylamino (e.g. benzylamino), or a heteroaryl $C_{1-3}$ alkylamino group where the heteroaryl ring contains one heteroatom (e.g. 3- or 4-pyridylmethyl); or $R_4$ represents the group $N=CHR_{13}$ where $R_{13}$ is a phenyl or pyridyl (e.g. 3- or 4- pyridyl) group; or $R_4$ represents $(CH_2)_qR_6$ where q is zero, 1, 2, or 3; and $R_6$ is nitro, cyano, heteroaryl (e.g. pyridyl or thienyl), $-CH_2NHC(=A)NHR_7$ where A is NCN or $CHNO_2$ and $R_7$ is $C_{1-3}$ alkyl (e.g. methyl); or the group $SO_2R_{15}$ where $R_{15}$ is hydroxy, $C_{1-3}$ alkyl (e.g. methyl), or aryl (e.g. phenyl); or the group $COR_{18}$ where $R_{18}$ is hydrogen, hydroxy, $C_{1-3}$ alkoxy (e.g. ethoxy), $C_{1-3}$ alkyl (e.g. methyl) or the group $NR_{19}R_{20}$ where $R_{19}$ and/or $R_{20}$ are hydrogen or $C_{1-3}$ alkyl (e.g. methyl), or $NR_{19}R_{20}$ forms a 5- or 6-membered ring (e.g. pyrrolidino); or the group $CH=NR_{22}$ where $R_{22}$ is hydroxy or $C_{1-3}$ alkoxy (e.g. methoxy): or $R_6$ is the group $NHR_9$ where $R_9$ is the group $SO_2R_{10}$ where $R_{10}$ represents $C_{1-3}$ alkyl (e.g. methyl), or phenyl optionally substituted by a $C_{1-3}$ alkyl (e.g. methyl) or $C_{1-3}$ alkoxy (e.g. methoxy) group; or $R_9$ represents $COR_{11}$ where $R_{11}$ represents hydrogen, $C_{1-3}$ alkyl (e.g. methyl or ethyl), $C_{1-3}$ alkoxy (e.g. methoxy or ethoxy), halomethyl (e.g. trifluoromethyl), phenyl $C_{1-3}$ alkyl (e.g. benzyl), furyl, pyridyl, thiazolyl, thienyl, phenyl optionally substituted by a $C_{1-3}$ alkyl (e.g. methyl) or $C_{1-3}$ alkoxy (e.g. methoxy) group, or $NHR_{12}$ where $R_{12}$ is $C_{1-3}$ alkyl (e.g. methyl), $C_{5-7}$ cycloalkyl (e.g. cyclohexyl) or phenyl optionally substituted by a $C_{1-3}$ alkyl (e.g. methyl) or $C_{1-3}$ alkoxy (e.g. methoxy) group; or $R_3$ and $R_4$ together represent $-(CH=CH)_2$ or $-(CH_2)_4-$.

In particular the groups $R_1$ to $R_4$ may have the meanings as follows:

$R_1$: $C_{1-7}$ alkyl, $C_{1-4}$ alkyl substituted by trifluoromethyl, $C_{2-4}$ alkyl substituted by hydroxy or di-$C_{1-3}$ alkylamino, $C_{5-7}$ cycloalkyl, alkenyl, phenyl $C_{1-3}$alkyl or heteroaryl $C_{1-3}$ alkyl where the heteroaryl ring contains one heteroatom (e.g. furylmethyl);

$R_2$: hydrogen or methyl; or $R_1R_2N$ may represent a 5 to 7 membered ring optionally containing a double bond or an alkyl (e.g. methyl) substituent; preferably $R_1R_2N$ represents dimethylamino or piperidino;

$R_3$: methyl, ethyl or 2-hydroxyethyl, preferably methyl;

$R_4$: hydrogen, $C_{1-4}$ alkyl, nitro, $C_{1-3}$ alkylthiomethyl, $C_{1-3}$ alkoxy $C_{1-4}$ alkyl, $C_{2-4}$ alkanoyloxy $C_{1-4}$ alkyl, phenyl $C_{1-3}$ alkyl, heteroarylmethyl (e.g. pyridylmethyl), the group $N=CHR_{13}$ where $R_{13}$ is phenyl or pyridyl, or the group $(CH_2)_qR_6$ where q is zero, 1, 2 or 3, and $R_6$ is hydroxy, cyano, $CH_2NHC(=A)NHR_7$ (where A is NCN or $CHNO_2$ and $R_7$ is $C_{1-3}$ alkyl); or $R_6$ represents the group $NHR_9$ where $R_9$ is hydrogen, $SO_2R_{10}$ where $R_{10}$ is $C_{1-3}$ alkyl, or $COR_{11}$ where $R_{11}$ is hydrogen, $C_{1-3}$ alkyl, $C_{1-3}$ alkoxy, benzyl, phenyl or $NHR_{12}$ (where $R_{12}$ is phenyl); or $R_6$ represents the group $SO_2R_{15}$ where $R_{15}$ is $C_{1-3}$ alkyl or aryl; or $R_6$ represents the group $COR_{18}$ where $R_{18}$ is hydrogen, hydroxy or $NR_{19}R_{20}$ where $R_{19}$ and/or $R_{20}$ are hydrogen or $C_{1-3}$ alkyl, or $NR_{19}R_{20}$ forms a 5- or 6- membered ring; or $R_6$ represents —CH=NOH; or $R_3$ and $R_4$ together represents $+CH=CH+_2$ or —$(CH_2)_4$—.

The group Alk preferably contains 1–4 carbon atoms and may be for example a methylene, ethylene or propylene group. More preferably Alk represents methylene.

Q is preferably a benzene ring in which incorporation into the rest of the molecule is through bonds at the 1- and 3- positions, or a furan ring optionally containing a further substituent $R_5$ or a thiophen ring containing a further substituent $R_5$, where $R_5$ is $C_{1-4}$ alkyl (e.g. methyl); more preferably Q is a benzene ring which is incorporated into the rest of the molecule through bonds in the 1- and 3- positions.

Preferably the chain —$X(CH_2)_nY(CH_2)_m$— contains from 4 to 6 atoms. When Q is an optionally substituted furan or thiophen, X preferably represents a bond and either Y is —S— or —$CH_2$—, n is 1 and m is 2 or Y is —O—, n is 1 and m is 3. More preferably Q is furan without a further substituent $R_5$, Y is —S—, n is 1 and m is 2. When Q is benzene, e.g. 1,3-benzene, X preferably represents a bond, Y is —O—, n is zero and m is 3, 4 or 5, or X and Y both represent —O— and n and m are both 2; more preferably Y is —O—, n is zero and m is 3 or 4.

A preferred group of compounds of formula (I) are those of formula (II).

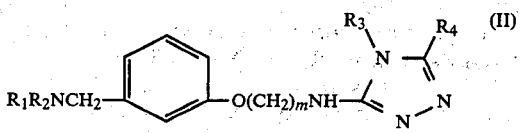

where $R_1$ and $R_2$ are methyl groups or together with the nitrogen atom to which they are attached form a pyrrolidino, piperidino or hexamethylenimino group (more preferably piperidino); m is 3 or 4, $R_3$ is methyl and $R_4$ is hydrogen, $C_{1-4}$ alkyl (e.g. methyl), $C_{2-4}$ alkanoyloxyalkyl (e.g. acetoxymethyl), $C_{1-3}$ alkylthiomethyl (e.g. methylthiomethyl), cyanoalkyl (e.g. cyanomethyl), or the group $(CH_2)_qR_6$ where q is zero, 1 or 2, and $R_6$ is hydroxy, $CH_2NHC(=CHNO_2)NHR_7$ (where $R_7$ is $C_{1-3}$ alkyl e.g. methyl), or the group $NHR_9$ where $R_9$ is hydrogen, $SO_2R_{10}$ (where $R_{10}$ is $C_{1-3}$ alkyl e.g. methyl) or $COR_{11}$ (where $R_{11}$ is $C_{1-3}$ alkyl e.g. methyl) or $R_6$ is the group $SO_2R_{15}$ where $R_{15}$ is $C_{1-3}$ alkyl (e.g. methyl) or $R_6$ is the group $COR_{18}$ where $R_{18}$ is hydrogen, hydroxy or amino; or $R_6$ is the group CH=NOH; or $R_3$ and $R_4$ together represent $+CH=CH+_2$ or —$(CH_2)-_4$.

Particularly preferred compounds are:
4-methyl-N-[3-[3-(1-piperidinylmethyl)phenoxy]-propyl]4H-1,2,4-triazole-3-amine
4-methyl-5-[4-[3-(1-piperidinylmethyl)phenoxy]-butyl]amino-4H-1,2,4-triazole-3-methanol
N-[3-[3-(1-piperidinylmethyl)phenoxy]propyl]-1,2,4-triazolo[4,3-a]pyridine-3-amine
4-methyl-5-[[3-[3(1-piperidinylmethyl)phenoxy]-propyl]amino]-4H-1,2,4-triazole-3-acetamide
4-methyl-5-[[3-[3-(1-piperidinylmethyl)phenoxy]-propyl]amino]-4H-1,2,4-triazole-3-methanol
4-methyl-5-(methylsulphonyl)methyl-N-[3-[3-(1-piperidinylmethyl)phenoxy]propyl]-4H-1,2,4-triazole-3-amine and their physiologically acceptable salts.

The invention includes the compounds of formula (I) in the form of physiologically acceptable salts with inorganic and organic acids. Particularly useful salts include hydrochlorides, hydrobromides, sulphates, methanesulphonates, acetates, maleates, succinates citrates, tartrates, fumarates and benzoates. The compounds of formula (I) and their salts may also form hydrates, which hydrates are also to be considered as part of the invention. The compounds of formula (I) can exhibit tautomerism and the formula is intended to cover all tautomers. Where optical isomers may exist the formula is intended to cover all diastereoisomers and optical enantiomers.

The compounds according to the invention, preferably in the form of a salt may be formulated for administration in any convenient way and the invention includes within its scope pharmaceutical compositions containing at least one compound according to the invention adapted for use in human or veterinary medicine. Such compositions may be formulated in a conventional manner using one or more pharmaceutically acceptable carriers or excipients. Such compositions may also contain if required other active ingredients e.g. $H_1$-antagonists.

Thus the compounds according to the invention may be formulated for oral, buccal, topical, parenteral or rectal administration. Oral administration is preferred.

For oral administration, the pharmaceutical compositions may take the form of for example, tablets, capsules, powders, solution, syrups or suspensions prepared by conventional means with acceptable excipients. For buccal administration the composition may take the form of tablets or lozenges formulated in conventional manner.

The compounds of the invention may be formulated for parenteral administration by bolus injection or continuous infusion. Formulations for injection may be presented in unit dosage form in ampoules, or in multidose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution with a suitable vehicle, e.g. sterile pyrogen-free water before use.

The compounds of the invention may also be formulated in rectal compositions such as suppositories or retention enemas, e.g. containing conventional suppository bases such as cocoa butter or other glyceride.

For topical application, the compounds of the invention may be formulated as ointments, creams, gels, lotions, powders or sprays in a conventional manner.

For internal administration a convenient daily dosage regime of the compounds according to the invention would be 1 to 4 doses to the total of some 5 mg to 1 g per day, preferably 5 to 250 mg per day, dependent upon the condition of the patient.

It will be appreciated that in the methods for the preparation of compounds of formula (I) given below, for certain reaction steps it may be necessary to protect various reactive substituents in the starting materials for a particular reaction and subsequently to remove the protecting group. Such protection and subsequent deprotection may be particularly pertinent where $R_1$ and/or $R_2$ in intermediates used to prepare compounds of formula (I) are hydrogen atoms and/or when R₃ in intermediates is an alkyl group bearing a hydroxy substituent and/or when R₄ in certain intermediates is an alkyl group bearing a hydroxyl or a primary or secondary amino substituent. Standard protection and deprotection procedures can be employed. For example an amino group may be protected by formation of a phthalimide which may subsequently be cleaved by treatment with a hydrazine e.g. hydrazine hydrate or a primary amine, for example methylamine.

In describing the processes which may be used for preparing the compounds of formula (I) or intermediates useful in the preparation thereof, any of $R_1$ to $R_{22}$, Alk, Q, X, Y, n and m in the various formulae are as defined in formula (I) unless otherwise stated.

Compounds of formula (I) in which R₄ is other than $(CH_2)qN=CR_{13}R_{14}$, alkoxy, acyloxyalkyl, nitro, $SO_2R_{15}$, $COR_{18}$ (where $R_{18}$ is hydrogen, aryl or aralkyl) or the group $CR_{21}=NR_{22}$ may be prepared by cyclisation of a compound of formula (III)

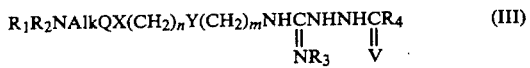
(III)

in which V is oxygen, sulphur or NH. When V represents sulphur then tautomerism with the adjacent NH group is possible (i.e.

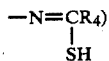

and the —SH group may be alkylated under standard conditions to form the group

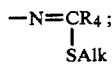

the S-alkylated compound may also be used in the cyclisation process.

The cyclisation may be carried out in the absence or presence of a solvent (e.g. dimethylformamide), or under basic conditions (e.g. using aqueous potassium hydroxide), at elevated temperatures (e.g. within the range 80°-150° C.).

In a convenient embodiment of the cyclisation process the intermediate (III) in which V is oxygen may be formed in situ by reacting an aminoguanidine of formula (IV)

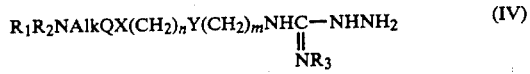
(IV)

with an acid $R_4CO_2H$ or an activated derivative thereof such as an acid halide (e.g. $R_4COCl$) or a trialkylorthoester (e.g. $R_4C(OEt)_3$). The reaction may be carried out as described above, and under these conditions cyclisation occurs to give a compound of formula (I).

In another embodiment of the cyclisation process an aminoguanidine of formula (IV) may be reacted with an alkali metal (E.g. potassium) isocyanate or isothiocyanate in a solvent such as acetonitrile at for example 20° C. to give an intermediate of formula (III) in which R₄ is amino and V is respectively oxygen or sulphur. Subsequent cyclisation then affords a compound of formula (I) in which R₄ is amino.

Compounds of formula (I) in which R₄ is other than $(CH_2)qN=CR_{13}R_{14}$ may be prepared by reducing a compound of formula (V)

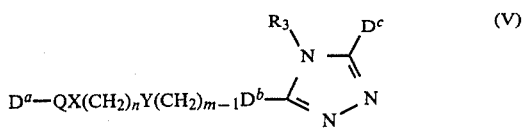
(V)

in which
$D^a$ may represent $R_1R_2NAlk$ or a group convertible thereto under reducing conditions;
$D^b$ represents —CH₂NH—, —CONH— or —CH=N—; and
$D^c$ represents R₄ or a group convertible thereto under reducing conditions, provided that at least one of $D^a$, $D^b$ and $D^c$ represents a reducible group and the other(s) take the appropriate meaning corresponding to formula (I).

Thus for example compounds of formula (I) may be prepared by reduction of a compound of formula (V) in which $D^a$ is $R_1R_2NAlk$, $D^b$ is —CONH— or —CH=N— and $D^c$ represents R₄ or a group convertible thereto under the conditions of the reduction reaction such as an ester group $(CH_2)_{q-1}CO_2R^a$ where $R^a$ is alkyl. Reduction may for example be carried out with lithium aluminium hydride in a suitable solvent such as tetrahydrofuran at for example 20° C. to reflux, or with sodium borohydride in a suitable solvent such as ethanol at 20°-50° C.

Compounds of formula (I) in which R₄ is the group $(CH_2)_qR_6$ where $R_6$ is $NR_8COR_{11}$, $NR_8SO_2R_{10}$, $CH_2NHC(=A)NHR_7$ or $N=CR_{13}R_{14}$ may be prepared by treating an aminoalkyltriazole of formula (VI)

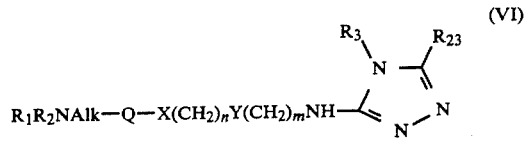
(VI)

in which $R_1$, $R_2$ and $R_3$ are as defined in formula (I) or are groups readily convertible thereto, and $R_{23}$ is the group $(CH_2)_qNHR_8$, the group $(CH_2)_{q+1}NH_2$ or the group $(CH_2)_qNH_2$, with a compound capable of replacing the hydrogen atom in the group NHR₈ by the group $COR_{11}$ or $SO_2R_{10}$ or a hydrogen atom in the group NH₂ of the group $(CH_2)_{q+1}NH_2$ by the group $C(=A)NHR_7$ or both hydrogen atoms in the group NH₂ of the group $(CH_2)_qNH_2$ by the group $=CR_{13}R_{14}$.

Thus for example the aminoalkyltriazole (VI) in which $R_{23}$ is the group $(CH_2)_q NHR_8$ may be reacted with an isocyanate $R_{12}'$ NCO in which $R_{12}'$ has any of the meanings defined for $R_{12}$ in formula (I) except hydrogen or represents an alkali metal atom such as potassium or sodium, or with an activated derivative of either a carboxylic acid $R_{11}COOH$ (in which $R_{11}$ is other than the group NHR₁₂) or a sulphonic acid $R_{10}SO_3H$ to give a compound of formula (I) in which R₆ is respectively the group $NR_8CONHR_{12}$, $NR_8COR_{11}$ (in which $R_{11}$ is other than NHR₁₂), or $NR_8SO_2R_{10}$.

Suitable activated derivatives include acid halides e.g. acid chlorides, alkylchloroformates, acid anhydrides including mixed anhydrides (e.g. acetic formic anhydride), and esters such as alkyl esters and ortho esters.

The reaction with an acid halide is preferably carried out in the presence of a base e.g. an inorganic base such as sodium hydroxide or an organic base such as triethylamine or pyridine. The reaction with an alkylchloroformate is preferably carried out in the presence of a base, e.g. potassium carbonate or triethylamine, in a solvent such as dimethylformamide. The reaction with an acid anhydride may be carried out in the absence of presence of solvent such as pyridine.

In the reaction with an isocyanate compound of formula (I) in which $R_{12}$ is other than hydrogen are conveniently prepared by carrying out the reaction in a solvent such as acetonitrile at temperatures from ambient to reflux. Compounds of formula (I) in which $R_{12}$ is hydrogen may be prepared by heating a salt e.g. hydrochloride of the aminotriazole (VI) with an aqueous solution of an appropriate cyanate e.g. potassium cyanate.

As a further embodiment of this process an aminoalkyltriazole (VI) in which $R_{23}$ is the group $(CH_2)_{q+1}NH_2$ may be treated with a compound of formula $LC(=A)NHR_7$ where L is a leaving group (e.g. methylthio) to give a compound of formula (I) in which $R_6$ is $CH_2NHC(=A)NHR_7$. The reactants may for example be mixed in an aqueous solution at room temperature to 100° C.

In yet another embodiment of this process an aminoalkyltriazole (VI) in which $R_{23}$ is the group $(CH_2)_qNH_2$ is treated with an appropriate aromatic aldehyde, e.g. benzaldehyde, or a ketone $R_{13}R_{14}CO$ optionally in the presence of a catalyst (e.g. p-toluenesulphonic acid) to give a product in which $R_6$ is $N=CR_{13}R_{14}$.

Compounds of formula (I) in which $R_4$ is an acyloxyalkyl group may be prepared by treating the corresponding hydroxyalkyl compound with an activated derivative (e.g. an acid chloride) of an appropriate acid. The reaction may be carried out at room temperature, optionally in the presence of a solvent (e.g. pyridine, tetrahydrofuran, acetone or dimethylformamide), and preferable in the presence of a base (e.g. pyridine, triethylamine or an alkali metal carbonate such as potassium carbonate).

Compounds of formula (I) in which $R_4$ is a nitro group or $R_3$ and $R_4$ together represent $-(CH=CH)_2$ may be prepared by heating a diamine of formula (VII)

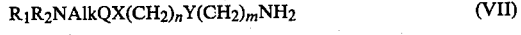
$$R_1R_2NAlkQX(CH_2)_nY(CH_2)_mNH_2 \quad (VII)$$

with an appropriate triazole of formula (VIII)

(VIII)

where P is a leaving group such as halogen, e.g. bromine, and $R_4$ represents nitro, or $R_3$ and $R_4$ together represent $-(CH=CH)_2$. The reaction may be carried out in the absence or presence of a solvent such as acetonitrile or an alcohol (e.g. ethanol).

The nitrotriazoles (VIII, $R_4=NO_2$), such as the bromonitrotriazole in which P is bromine, may be prepared from the corresponding triazole of formula (VIII) in which P is hydrogen, for example by treatment with bromine.

Compounds of formula (I) in which $R_3$ and $R_4$ together represent $-(CH_2)_4-$ may be prepared by reduction of the corresponding compound in which $R_3$ and $R_4$ together represent $-(CH=CH)_2$ using for example hydrogen and a metal catalyst (e.g. platinum) in a solvent such as ethanol.

Compounds of formula (I) in which $R_4$ is the group $(CH_2)_qR_6$ in which $R_6$ is $COR_{18}$ (where $R_{18}$ is hydrogen, alkyl, aryl or aralkyl) or $SO_2R_{15}$ may be prepared by oxidation of the corresponding compound in which $R_4$ is the group $(CH_2)_qCHR_{18}OH$, $(CH_2)_qSR_{15}$ (where $R_{15}$ is other than hydroxy) or $(CH_2)_qSH$.

Thus aldehydes and ketones of formula (I) in which $R_4$ is the group $(CH_2)_qCOR_{18}$ where $R_{18}$ is hydrogen, alkyl, aryl or aralkyl may be prepared by oxidising the corresponding hydroxyalkyl compound in which $R_4$ is $(CH_2)_qCHR_{18}OH$ using for example oxalyl chloride and dimethylsulphoxide in a solvent such as dichloromethane at reduced temperature (e.g. $-50°$ C.) or using activated manganese dioxide in a solvent such as chloroform at for example room temperature.

Compounds of formula (I) in which $R_4$ is the group $(CH_2)_qSO_2R_{15}$ may be prepared by oxidising the corresponding compound in which $R_4$ is either $-(CH_2)_qSR_{15}$ (where $R_{15}$ is other than hydroxy) or $(CH_2)_qSH$ with for example peracetic acid or nitric acid. The reaction may be carried out in a solvent such as acetic acid, at room temperature.

The starting material in which $R_4$ is $(CH_2)_qSH$ where q is other than zero may be obtained by alkaline hydrolysis of the corresponding isothiourea, which may in turn be prepared by alkylating thiourea with an appropriate compound of formula (I) in which $R_6$ is a leaving group e.g. halo.

The thiol starting material in which $R_4$ is SH may be prepared by diazotisation of the corresponding aminotriazole followed by treatment with an alkali metal (e.g. potassium) salt of ethyl xanthate to give a xanthate in which $R_4$ is the group $-SC(=S)OEt$, which is subsequently hydrolysed (for example by heating with ethanolic potassium hydroxide) to give the starting thiol in which $R_4$ is the group SH.

The above oxidation process is particularly applicable to the preparation of compounds of formula (I) in which Q is a benzene or furan ring, X and Y are each oxygen, methylene or a bond, and there is no unsaturation within the groups $R_1$ and $R_3$.

Compounds of formula (I) in which $R_4$ is $(CH_2)_qCR_{21}=NR_{22}$ may be prepared by reacting the corresponding carbonyl compound i.e. a compound of formula (I) in which $R_4$ is $(CH_2)_qCOR_{21}$, with an appropriate reagent $H_2NR_{22}$ in a suitable solvent such as ethanol, optionally with heating.

Compounds of formula (I) in which $R_4$ is $(CH_2)_qR_6$ where $R_6$ is $SO_2NR_{16}R_{17}$ or $CONR_{19}R_{20}$ may be prepared by reacting an activated derivative of the corresponding carboxylic acid or sulphonic acid, i.e. compounds of formula (I) in which $R_4$ is $(CH_2)_qR_6$ where $R_6$ is $CO_2H$ or $SO_3H$, with ammonia or an appropriate amine $HNR_{16}R_{17}$ or $HNR_{19}R_{20}$. Suitable activated derivatives include those referred to previously e.g. acid chlorides and esters.

Compounds of formula (I) in which $R_4$ is $(CH_2)_qR_6$ where $R_6$ is $-CONH_2$ or $-CO_2H$ may be prepared by hydrolysis of the corresponding nitrile.

Compounds of formula (I) in which $R_4$ is $(CH_2)_q R_6$ where $R_6$ is cyano may be prepared by heating the corresponding oxime of formula (I) in which $R_6$ is —CH=NOH with a dehydrating agent such as acetic anhydride.

Aldehydes of formula (I) in which $R_4$ is $(CH_2)_q R_6$ where $R_6$ is CHO may be prepared by reducing the corresponding nitrile in which $R_4$ is $(CH_2)_q CN$ with for example hydrogen in the presence of Raney nickel. The resulting aldehyde may be conveniently isolated as its semicarbazone, from which the desired aldehyde may be generated by treatment with hydrochloric acid and aqueous formaldehyde.

The aminoguanidine (III) may be prepared, for example by reacting a diamine of formula (VII) with a compound of formula (IX)

where L is a leaving group such as thioalkyl, e.g. thiomethyl.

The triazoles of formula (V) may be prepared by reacting a triazole of formula (X)

with a compound of formula (XI)

where G is $CO_2H$ or CHO.

The triazoles of formula (X) may in general be prepared by the method described by C. F. Kroger, Chem. Berichte, 1964, 97, 396.

Amines of formula (VII) may be made by methods analogous to those described in German Offenlegungsschrifts 2734070, 2821410 and 2821409 and in European Patent Specification publication No. 0029306.

Where the product of any of the above processes is a free base and a salt is required, the salt may be formed in a conventional manner. Thus, for example, a generally convenient method of forming the salts is to mix appropriate quantities of the free base and the acid in an appropriate solvent(s) e.g. an alcohol such as ethanol or an ester such as ethyl acetate.

The invention is illustrated but not limited by the following Examples and Preparations.

PREPARATION 1

N-Amino-N'-methyl-N''-[3-[3-(1-piperidinylmethyl)-phenoxy]propyl]guanidine hydroiodide A mixture of 3-[3-(1-piperidinylmethyl)phenoxy]-propanamine (12.4 g) and methyl N-methylhydrazine carboximidothioate (12.55 g) were heated as a solution in water (40 ml) at 65° for 6 h. The cooled mixture was stirred, and purged with nitrogen for 14 h. The water was decanted from the solid which was dissolved in ethyl acetate (50 ml) and saturated sodium carbonate solution (50 ml). The aqueous solution was further extracted with ethyl acetate. The combined organic extracts were dried and evaporated to leave a red oil. This oil was triturated with cyclohexane to give the title compound as a pale pink solid (11.8 g) m.p.=104°–108° C.

PREPARATION 2

Methyl, 5-amino-4-methyl-4H-1,2,4-triazole-3-carboxylate

N-amino-N'-methyl guanidine hydroiodide (4.3 g) and oxalic acid dihydrate (2.5 g) were heated at reflux in water (25 ml) for 3.5 h. The reaction was cooled, basified with excess solid potassium hydroxide, and heated on a steambath for 2 h. The reaction was cooled and acidified to pH 3 with conc. hydrochloric acid to produce a white solid (1.6 g) which was used without further purification. This solid (8 g), in dry methanol (100 ml) was saturated with hydrogen chloride gas at 5°, and then heated at reflux for 4 h. The solvent was evaporated and the residue was dissolved in water. The pH of the solution was adjusted to pH 7 with solid potassium carbonate to precipitate the title compound as a white solid (2.7 g) which was crystallised from methanol, m.p. 208°–9°.

PREPARATION 3

Methyl 4-methyl-5-[[1-oxo-4[3-(1-piperidinylmethyl)phenoxy]-butyl]amino]-4H-1,2,4-triazole-3-carboxylate Thionyl chloride (2.5 ml) was added to a solution of 4-[3-(1-piperidinylmethyl)phenoxy]butanoic acid (2.77 g) in dry dichloromethane (30 ml) and dry dimethylformamide (6 drops). The reaction was stirred at room temperature for 2 h, and the solvent was removed in vacuo. Excess thionyl chloride was removed by azeotropic distillation with toluene (3×15 ml). The residue was dissolved in dry dimethylformamide (50 ml), and methyl 5-amino-4-methyl-4H-1,2,4-triazole-3-carboxylate (1.53 g) was added. The solution was stirred at room temperature for 18 h, heated at 60° for 3 h, and the solvent removed under reduced pressure to leave a brown gum. This gum was partitioned between aqueous sodium carbonate solution and ethyl acetate. Evaporation of the organic phase gave a viscous oil which was triturated with a mixture of ether and light petroleum b.p. 60°–80° to give a solid. This solid was recrystallised from a mixture of ethyl acetate and light petroleum b.p. 60°–80° to give the title compound as an off-white solid (0.68 g) m.p. 108°–109.5°.

PREPARATION 4

Methyl N'-[2-[[5-[(Dimethylamino)methyl]-2-furanylmethyl]-thio]ethyl]-N-methylcarbamimidothioate A solution of N-[2-[[5-[(dimethylamino)methyl]-2-furanmethyl]thio]ethyl]-N'-methylthiourea (5.75 g) in methanol (30 ml) was just acidified with hydrogen chloride in ether. The ether was evaporated in vacuo, methyl iodide (3.12 g) added and the solution heated under reflux for 1.25 hours. The solution was evaporated in vacuo, the oily residue dissolved in water (30 ml) and an excess of anhydrous sodium carbonate added. The oily suspension was extracted with ethyl acetate (2×40 ml), dried (MgSO$_4$), decolorised with charcoal, filtered and evaporated to give the title compound (5 g) as an oil.

Found: C, 52.0; H, 7.9; N, 13.9 $C_{13}H_{23}N_3OS_2$ requires C, 51.8; H, 7.7; N, 14.0%

EXAMPLE 1

4-Methyl-N-[3-[3-(1-piperidinylmethyl)phenoxy]-propyl]-4H-1,2,4-triazole-3-amine A mixture of 3-[3-(1-piperidinylmethyl)phenoxy]-propylamine (2.48 g) and methyl N-methyl hydrazine carboximidothioate (2.48 g) was heated as a melt at 60° during 4 h. The residue was dissolved in formic acid (50 ml) and the solution was heated under reflux during 12 h. The cooled solution was diluted with water (100 ml) and the pH was adjusted to pH 9 with anhydrous potassium carbonate. The mixture was extracted with ethyl acetate. The combined extracts were evaporated to give an orange oil. The oil was heated at 150° during 0.5 h and the unwanted material distilled off a 180° C. 0.06 mm Hg leaving a yellow oil.

This oil was crystallised from ethyl acetate. The solid was discarded. The mother liquors were concentrated to give an orange oil which was triturated in a mixture of ethyl acetate (10 ml) and ether (20 ml) to give the title compound as a white powder (200 mg) m.p. 118°–9°.

Assay Found: C, 65.87; H, 8.23; N, 20.99, $C_{18}H_{27}N_5O$ Requires: C, 65.65; H, 8.21; N, 21.28%.

EXAMPLE 2

4,5-Dimethyl-N-[3-[3-(1-piperidinylmethyl)phenoxy]-propyl]-4H-1,2,4-triazole-3-amine N-Amino-N'-methyl-N''[3-[3-(1-piperidinylmethyl)-phenoxy]propyl]guanidine hydroiodide (3.19 g) and glacial acetic acid (50 ml) were heated at reflux for 2 h. The cooled reaction solution was basified with 2N sodium hydroxide, and extracted with ethyl acetate. The organic extracts were evaporated to leave a pale yellow oil. This oil was extracted with boiling cyclohexane (150 ml) and insoluble solid that remained was further extracted with boiling ether (50 ml) to leave a crystalline white solid. This solid was recrystallised from ethyl acetate to give the title compound as a white solid (0.46 g) m.p.=143°–4° C.

Assay Found: C, 65.92; H, 8.34; N, 19.96, $C_{19}H_{29}N_5O$ Requires: C, 66.44; H, 8.51; N, 20.39.

EXAMPLE 3

4-Methyl-5-[[4-[3-(1-piperidinylmethyl)phenoxy]butyl]amino]-4H-1,2,4-triazole-3-methanol Lithium aluminium hydride (0.46 g) was added to a solution or methyl 4-methyl-5-[[1-oxo-4[3-(1-piperidinylmethyl)phenoxy]butyl]amino]-4H-1,2,4-triazole-3-carboxylate (0.58 g) in dry tetrahydrofuran (20 ml) under an atmosphere of dry nitrogen. The grey suspension was stirred at room temperature for 3.5 h before adding water (0.5 ml), 15% aqueous sodium hydroxide (1.0 ml), water (0.5 ml) and ethyl acetate (20 ml). The suspension was filtered and the filtrate was evaporated under reduced pressure to give a solid which was recrystallised from ethyl acetate (5 ml) to give the title compound as a white solid (0.04 g) m.p. 128°–30°.

Analysis Found: C, 63.7; H, 8.2; N, 18.4; $C_{20}H_{31}N_5O_2$ requires: C, 64.3; H, 8.4; N, 18.7%.

EXAMPLE 4

(a)

N-[3-[3-(1-piperidinylmethyl)phenoxy]propyl]-1,2,4-triazolo-[4,3-a]pyridine-3-amine 3-Bromo-1,2,4-triazolo[4,3-a]pyridine (2.5 g), 3-[3-(1-piperidinylmethyl)phenoxy]propanamine (9 g) and ethanol (20 ml) were heated in an autoclave at 110° for 24 h and then at 150° for 36 h. The mixture was evaporated in vacuo (200°, 0.1 mm Hg) and the residue (2.3 g) was chromatographed on silica using dichloromethane:ethanol:880 ammonia (100:8:1) to give a gum which was crystallised from methyl acetate-petroleum ether (b.p. 60°–80°) to give the title compound (0.8 g) as white crystals, m.p. 150°–151°.

Found: C, 69.0; H, 7.4; N, 19.1; $C_{21}H_{27}N_5O$ requires: C, 69.0; H, 7.45; N, 19.2%.

(b) In a similar manner 3-bromo-1,2,4-triazolo[4,3-a]pyridine (0.8 g) and 3-[3-(dimethylaminomethyl)-phenoxy]propanamine (0.92 g) gave N-[3-[3-(dimethylaminomethyl)phenoxy]propyl]-1,2,4-triazolo[4,3-a]pyridine-3-amine (67 mg) as white crystals, m.p. 143°–45°.

NMR (CDCl₃): 2.2, dd, (1H); 2.5, dd, (1H); 2.65–3.5, m, (6H); 5.86, t, (2H); 6.22, q, (2H); 6.62, s, (2H); 7.73, s, (6H); 7.75, m, (2H).

EXAMPLE 5

N-[3-[3-(1-Piperidinylmethyl)phenoxy]propyl]-(5,6,7,8-tetrahydro-1,2,4-triazolo[4,3-a]pyridine)-3-amine hydrate (4:1)

A solution of N-[3-[3-(1-piperidinylmethyl)phenoxy]-propyl]-1,2,4-triazolo[4,3-a]pyridine-3-amine (475 g) in ethanol was hydrogenated at atmospheric pressure over platinum on carbon. The resulting mixture was filtered and evaporated to a gum which crystallised from isopropanol/ethyl acetate to give the title compound as fibrous white needles (382 mg) m.p. 164°–5°.

Analysis Found: C, 67.5; H, 8.5; N, 18.5; $C_{21}H_{31}N_5O.1/4H_2O$ requires: C, 67.4; H, 8.6; N, 18.7%.

EXAMPLE 6

(a)

4-Methyl-5-[[3-[3-(1-piperidinylmethyl)phenoxy]-propyl]amino]-4H-1,2,4-triazole-3-acetonitrile dioxalate sesquihydrate A mixture of N-amino-N'-methyl-N''[3-[3-(1-piperidinylmethyl) phenoxy]propyl]guanidine hydroiodide (4.5 g) and cyanoacetic acid (1.7 g) was heated at 100°–125° for 7 h. The cooled reaction mixture was basified with sodium carbonate and extracted with chloroform. The organic extract was evaporated to leave an oil which was chromatographed on silica using methanol. The resulting oil (0.56 g) was dissolved in ethanol and treated with an ethanolic solution of oxalic acid. Recrystallisations of the solid from a mixture of ethanol and water gave the title compound (0.45 g) as a white powder. m.p. 93°–97°.

Analysis Found: C, 50.0; H, 5.8; N, 14.2; $C_{20}H_{28}N_6.2H_2C_2O_4.1\frac{1}{2}H_2O$ requires: C, 50.1; H, 6.1; N, 14.6%.

(b) In a similar manner N-amino-N'-methyl-N''-[3-[3-(1-piperidinylmethyl)phenoxy]propyl]guanidine. hydroioidide (4.5 g) and methylthioacetic acid (2.13 g) gave, after chromatography on silica using ethylacetate:isopropanol:water:0.88 ammonia (25:15:8:2), 4-methyl-5-(methylthio) methyl-N-[3-[3-(1-piperidinylmethyl)phenoxy]propyl]-4H-1,2,4--triazole-3-amine (0.48 g) as a white solid, m.p. 104°–5°.

Analysis Found: C, 61.7; H, 8.0; N, 17.7; $C_{20}H_{31}N_5OS$ requires: C, 61.7; H, 8.0; N, 18.0%.

EXAMPLE 7

4-Methyl-5-[[3-[3-(1-piperidinylmethyl)phenoxy]-propyl]amino]-4H-1,2,4-triazole-3-acetamide A solution of 4-methyl-5-[[3-[3-(1-piperidinylmethyl)-phenoxy]propyl]amino]-4H-1,2,4-triazole-3-acetonitrile dioxalate (0.05 g) in 35% hydrochloric acid (1 ml) was heated at 40° C. for 3 h. The mixture was basified with sodium hydroxide and extracted with chloroform. Evaporation of the organic solution gave the title compound (0.01 g) as a white powder.

TLC Silica.Ethyl acetate:isopropanol:water:ammonia (25:15:8:2)$R_f$ 0.45

NMR (CDCl$_3$):2.53, br.s, (1H): 2.78, t, (1H); 3.00–3.3, m, (3H); 3.73, br.s, (1H); 4.72, br.t, (1H); 5.90, t, (2H); 6.3–6.63 s+q+s+s, (9H); 7.5–7.72, m+m, (6H); 8.30–8.65, m, (6H).

EXAMPLE 8

4-Methyl-5-[[3-[3-(1-piperidinylmethyl)phenoxy]-propyl]amino]-4H-1,2,4-triazole-3-methanol N-Amino-N'-methyl-N''-[3-[3-(1-piperidinylmethyl)-phenoxy]propyl]guanidine hydroiodide (2.24 g) and glycolic acid (1.52 g) were heated together for 3 h in dry benzene (25 ml) at reflux. The benzene was decanted from the residual oil, which was partitioned between ethyl acetate and aqueous 1N sodium hydroxide solution. The organic phase was chromatographed on silica using methanol to give a white solid. This solid was washed with boiling ethyl acetate to leave the title compound as a white solid (0.013 g) m.p. 151°–2°.

NMR (CDCl$_3$/DMSO): 2.8, t, (1H); 3.1–3.4, m, (3H); 5.1, t, (1H); 5.42, s, (2H); 6.0, t, (2H); 6.5, q, (2H); 6.6, s, (3H); 6.63, s, (2H); 7.7, m., (4H); 7.9, m, (2H); 8.5, m, (6H).

EXAMPLE 9

4-Methyl-5-(methylsulphonyl)methyl-N-[3-[3-(1-piperidinylmethyl)phenoxy]propyl-4H-1,2,4-triazole-3-amine Peracetic acid (0.82 ml of 6.1M) in acetic acid (4.5 ml) was added at 0° to a solution of 4-methyl-5-(methylthio)methyl-N-[3-[3-(1-piperidinylmethyl)phenoxy]-propyl]-4H-1,2,4-triazole-3-amine (0.63 g) and sodium acetate (0.39 g) in acetic acid (8 ml). The mixture was stirred at room temperature for 18 h. Excess peracetic acid was decomposed with sodium sulphite (1g) and the resulting suspension was evaporated. The residue was treated with water (10 ml), neutralised with sodium bicarbonate solution and extracted with ethyl acetate. The extract was evaporated to give the title compound as a white solid (0.58 g), m.p. 121°–3° C.

NMR (CDCl$_3$): 2.77, dd, (1H); 3.00–3.35, m, (3H); 5.50, t, (1H); 5.65, s, (2H); 5.83, t, (2H); 6.35, q, (2H); 6.56–6.58, s+s, (5H); 7.04, s, (3H); 7.60–7.83, m, (6H); 8.25–8.70, m, (6H).

EXAMPLE 10

4,5-Dimethyl-N-[2-[[5-[(dimethylamino)methyl]-2-furanylmethyl]thio]ethyl]-4H-1,2,4-triazole-3-amine.-dimaleate A mixture of methyl N'-[2-[[5-[(dimethylamino)methyl]-2-furanylmethyl]thio]ethyl]-N-methylcarbamimidothioate (4.5 g) and acetic acid hydrazide (0.89 g) was heated at 90° for 24 h. Column chromatography on silica using dichloromethane:ethanol:0.88 ammonia (100:8:1) gave a viscous oil (2.8 g). A portion of this oil (0.4 g) was treated with excess maleic acid in acetone to give the title compound as a white solid (0.35 g) m.p. 93°5°.

NMR (D$_2$O): 3.33, d, (1H); 3.63–3.70, d+s, (5H); 5.70, s, (2H); 6.20, s, (2H); 6.50–6.56, t+s, (5H); 7.15–7.18, s+t, (8h); 7.58, s, (3H).

EXAMPLE 11

4-Methyl-5-[[3-[3-(1-piperidinylmethyl)phenoxy]-propyl]amino]-4H-1,2,4-triazole-3-acetic acid monopotassium salt.dihydrate A solution of 4-methyl-5-[[3-[3-(1-piperidinylmethyl)-phenoxy]propyl]amino]-4H-1,2,4-triazole-3-acetonitrile. dioxalate (0.4 g) in 35% hydrochloric acid (10 ml) was heated at 40° for 3 h. The cooled solution was basified with 10% aqueous sodium carbonate solution and washed with chloroform. The aqueous solution was saturated with potassium carbonate and extracted with isopropanol. The extract was washed with saturated potassium carbonate, dried, and evaporated to leave a residue which was crystallised from ethyl acetate and methanol to give the title compound (0.16 g) as a white powder, m.pt. 166°–169°.

Analysis Found: C, 52.30; H, 6.77; N, 15.20; C$_{20}$H$_{28}$N$_5$O$_3$K.2H$_2$O requires: C, 52.05; H, 6.98; N, 15.18%.

EXAMPLE 12

4-Methyl-5-[[3-[3-(1-piperidinylmethyl)phenoxy]-propyl]amino]-4H-1,2,4-triazole-3-(2-ethanamine), trihydrochloride, monohydrate A solution of 4-methyl-5-[[3-[3-(1-piperidinylmethyl)-phenoxy]propyl]amino]-4H-1,2,4-triazole-3-acetonitrile dioxalate (0.65 g) in ethanol (25 ml) and 0.88 ammonia (2.5 ml), was hydrogenated at 70 p.s.i. over 5% rhodium on alumina (4 g) for 18 h. The mixture was filtered through 'hyflo', and the filtrate was evaporated. The residue was chromatographed on silica using methanol and 0.88 ammonia, to give a yellow gum (400 mg). A portion of this gum (200 mg) was dissolved in methyl acetate and ethanol, and treated with ethereal hydrogen chloride to precipitate a white solid which was recrystallised from isopropanol and ethanol to give the title compound as a white powder (87 mg) m.p. 221°–223°.

Analysis Found: C, 47.7; H, 7.2; N, 16.4; C$_{20}$H$_{32}$N$_6$O.3HCl.H$_2$O Requires: C, 48.0; H, 7.5; N, 16.8%.

EXAMPLE 13

N-[2-[4-Methyl-5-[[3-[3-(1-piperidinylmethyl)phenoxy]-propyl]amino]-4H-1,2,4-triazol-3-yl]ethyl]acetamide A mixture of 4-methyl-5-[[3-[3-(1-piperidinylmethyl)-phenoxy]propyl]amino-4H-1,2,4-triazole-3-(2-ethanamine) (0.16 g) and acetic anhydride (0.1 ml) in pyridine (10 ml) was stirred at 5° for 1 h. Evaporation gave an oil which was chromatographed on silica using methanol: 0.88 ammonia (79:1) to provide the title compound as a semi-solid (0.085 g)

NMR (CDCl$_3$): 2.78, dd, (1H); 3–3.34, m, (3H); 5.70–5.90, 2xt, (3H); 6.2–6.6, 2xt, (4H); 6.60, s, (2H); 6.75, s, (3H); 7.30, t, (2H); 7.6–7.87, 2xm, (7H); 8.10, s, (3H); 8.40–8.60, m, (6H);

TLC: Methanol: 0.88 Ammonia (79:1) Rf 0.41.

EXAMPLE 14

N-[2-[4-Methyl-5-[[3-[3-(1-piperidinylmethyl)phenoxy]propyl]amino]-4H-1,2,4-triazol-3-yl]ethyl]methanesulphonamide A mixture of 4-methyl-5-[[3-[3-(1-piperidinylmethyl)phenoxy]propyl]amino]-4H-1,2,4-triazole-3-(2-ethanamine) (0.38 g) and methanesulphonyl chloride (0.1 g) in dry pyridine was stirred at room temperature for 18 h. The mixture was diluted with ethanol evaporated in vacuo and the residue was partitioned between aqueous potassium carbonate and ethyl acetate. The organic layer was washed with brine and evaporated to give a brown gum which was chromatographed on alumina using dichloromethane:ethanol:0.88 ammonia (75:8:1) to give a gum. This gum on trituration with diethyl ether gave the title compound (0.13 g) as off-white solid. m.p. 105°–6°.

NMR (CDCl$_3$): 2.78, t, (1H); 3.00–3.33, m, (3H); 3.65, b, (1H); 5.68, t, (1H); 5.91, t, (2H); 6.20–6.55+6.59, m+s, (6H); 6.75, s, (3H); 7.05, s, (3H); 7.18, t, (2H); 7.50–8.0, m, (6H); 8.3–8.7, m, (6H):

EXAMPLE 15

4-Methyl-5-[[3-[3-(1-piperidinylmethyl)phenoxy]propyl]amino]-4H-1,2,4-triazole-3-carboxaldehyde Activated manganese dioxide (20 g) and 4-methyl-5-[[3-[3-(1-piperidinylmethyl)phenoxy]propyl]amino]-4H-triazole-3-methanol (2g) were stirred in chloroform (50 ml) at room temperature for 12 h. The mixture was filtered and the filtrate was evaporated to give an oil which was chromatographed on silica using ethyl acetate:ethanol (9:1) to give a gum. This gum was crystallised from methyl acetate:light petroleum (b.p. 60°–80°) (1:2) to give the title compound as white crystals (0.25 g) m.p. 157°–158°.

NMR (CDCl$_3$): 0.15, s, (1H); 2.8, t, (1H); 3–3.4, m, (3H); 4.7, brt, (1H); 5.93, t, (2H); 6.27–6.37, q+s, (5H); 6.6, s, (2H); 7.65–7.85, m, (6H); 8.55, m, (6H).

EXAMPLE 16

4-Methyl-5-[[3-[3-(1-piperidinylmethyl)phenoxy]propyl]amino]-4H-1,2,4-triazole-3-methanol acetate(ester)

Acetyl chloride (0.18 g) was added dropwise to a stirred solution of 4-methyl-5-[[3-[3-(1-piperidinylmethyl)phenoxy]propyl]amino]-4H-1,2,4-triazole-3-methanol (0.7 g) in pyridine (5 ml), and the reaction mixture was stirred at room temprature for 18 h. The solution was evaporated, excess aqueous sodium carbonate was added, and the mixture was extracted with ethyl acetate. The extract was washed with water, dried and evaporated to give the title compound as a white solid, (0.54 g) m.p. 95°–97°.

NMR (CDCl$_3$): 2.7–3.5, m, (4H); 4.94, s, (2H); 5.15, t, (1H); 5.95, t, (2H); 6.42, q, (2H); 6.61, s, (2H); 6.68, s, (3H); 7.5–8.0, m, (6H) overlain by 7.95, s, (3H); 8.3–8.6, m, (6H).

EXAMPLE 17

N-Methyl-N'-[2-[4-methyl-5-[[3-[3-(1-piperidinylmethyl)phenoxy]propyl]amino]-4H-1,2,4-triazol-3-yl]ethyl]-2-nitro-1,1-ethenediamine.

A solution of 4-methyl-5-[[3-[3-(1-piperidinylmethyl)phenoxy]propyl]amino]-4H-1,2,4-triazolo-3-(2-ethanamine) (0.38 g) and methyl N-methyl-2-nitroimidothioate (0.29 g) in methanol (5 ml) and water (10 ml) was stirred at room temperature for 24 h, and then at 50° for 5 h. The resulting solution was evaporated, treated with aqueous potassium carbonate and extracted with a mixture of ethyl acetate and isopropanol. The extract was washed with brine and evaporated to leave a gum which was chromatographed on alumina using dichloromethane:ethanol:0.88 ammonia (75:8:1) to give a gum. This gum on trituration with diethyl ether gave the title compound as an off-white solid. (0.06 g) m.p. 110°–112°

NMR (CDCl$_3$): 1.18, br.s, (2H); 2.78, t, (1H); 3.0–3.6, m+m, (4H); 5.48, br.t, (1H); 5.89, t, (2H); 6.15, m, (2H); 6.42, q, (2H); 6.58, s, (2H); 6.70, s, (3H); 7.15, m, (5H); 7.62–7.85, m+m, (6H); 8.3–8.65, m, (6H).

EXAMPLE 18

4-Methyl-5-[[3-[3-(1-piperidinylmethyl)phenoxy]propyl]amino]4H-1,2,4-triazole-3-carboxaldehyde oxime A solution of hydroxylamine hydrochloride (0.13 g) in ethanol (10 ml) was treated with potassium hydroxide (0.11 g). A solution of 4-methyl-5-[[3-[3-(1-piperidinylmethyl)phenoxy]propyl]amino]-4H-1,2,4-triazole-3-carboxaldehyde (0.54 g) in ethanol (10 ml) was added. The mixture was stirred at room temperature for 15 min and then filtered. The filtrate was evaporated and the residue was crystallised from a mixture of ethanol (5 ml) and ethyl acetate (5 ml) to give the title compound as a white crystalline solid (0.21 g) m.p. 187°–188°.

NMR (DMSO): −1.6, br.s, (1H); 1.92, s, (1H); 2.75, t, (1H); 3.0–3.3, m, (3H); 3.60, br.t, (1H); 5.91, t, (2H); 6.39, s, (3H); 6.50, q, (2H); 6.62, s, (2H); 7.50–7.78, m, (4H); 7.78–8.05, m, (2H); 8.30–8.65, m, (6H).

EXAMPLES OF PHARMACEUTICAL COMPOSITIONS

| Tablets | mg/tablet | mg/tablet |
|---|---|---|
| Active ingredient | 20.0 | 40.0 |
| Microcrystalline cellulose BPC | 99.5 | 199.0 |
| Magnesium stearate B.P. | 0.5 | 1.0 |
| Compression weight | 120.0 | 240.0 |

The drug is sieved through a 250 μm sieve, blended with the excipients and compressed using 6.5 mm and 8.0 mm diameter punches for the 20 and 40 mg strengths respectively. Tablets of other strengths may be prepared by increasing the compression weight and using punches to suit.

The tablets may be film coated with suitable film forming materials, e.g. methyl cellulose, ethyl cellulose or hydroxypropylmethyl cellulose, using standard techniques. Alternatively the tablets may be sugar coated.

INJECTION FOR INTRAVENOUS ADMINISTRATION

| | % w/v |
|---|---|
| Active ingredient | 0.25 |
| Water for Injections BP to | 100.00 |

Sodium chloride may be added to adjust the tonicity of the solution and the pH may be adjusted to that of maximum stability using dilute acid or alkali or suitable buffer salts.

The solution is prepared, clarified and filled under nitrogen into appropriate sized ampoules sealed by fusion of the glass. The injection is sterilised be heating in an autoclave using one of the acceptable cycles. Alternatively the solution may be sterilised by filtration and filled into sterile ampoules under aseptic conditions.

We claim:

1. A compound of the formula (I)

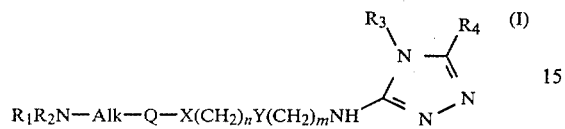

$$R_1R_2N\text{—Alk—Q—}X(CH_2)_nY(CH_2)_mNH$$

and physiologically acceptable salts and hydrates thereof, in which $R_1$ represents $C_{1-14}$ alkyl, $C_{3-8}$ cycloalkyl, $C_{3-6}$ alkenyl, $C_{3-6}$ alkynyl, aryl $C_{1-6}$ alkyl, trifluoro $C_{1-6}$ alkyl, heteroaralkyl wherein the heterocyclic portion is furyl, thienyl, pyrrolyl, pyridinyl, pyrimidinyl, triazinyl, oxazolyl, triazolyl or thiazolyl and the alkyl portion is a straight or branched $C_{1-4}$ alkyl chain or $C_{1-6}$ alkyl substituted by $C_{3-8}$ cycloalkyl, hydroxy, $C_{1-6}$ alkoxy, amino, $C_{1-6}$ alkylamino or di $C_{1-6}$ alkylamino; and $R_2$ represents hydrogen or a $C_{1-4}$ alkyl group; or $R_1$ and $R_2$ together with the nitrogen atom to which they are attached form a pyrrolidino, piperidino, hexamethylenimino, heptamethylenimino, tetrahydropyridino, 4-hydroxypiperidino, 4-$C_{1-3}$ alkylpiperidino, morpholino, 2,6-di-$C_{1-3}$ alkylmorpholino or a thiamorpholino group;

Alk represents a straight or branched alkylene chain of 1 to 6 carbon atoms;

Q represents a furan or thiophen ring in which incorporation into the rest of the molecule is through bonds at the 2- and 5-positions, the furan or thiophen ring optionally bearing a further substituent $R_5$ adjacent to the group $R_1R_2N$-Alk-, or Q represents a benzene ring in which incorporation into the rest of the molecule is through bonds at the 1- and 3- or 1- and 4-positions;

$R_5$ represents halogen or $C_{1-4}$ alkyl which may be substituted by hydroxy or $C_{1-4}$ alkoxy;

X and Y, which may be the same or different, each represent oxygen, sulphur, methylene or a bond;

n represents zero, 1, 2 and 3 and m represents an integer from 2 to 5 with the provisos that (a) the total number of atoms in the chain $X(CH_2)_nY(CH_2)_m$ is an integer from 3 to 8 and (b) when X and Y represent oxygen or sulphur then n is 2 or 3;

$R_3$ represents $C_{1-6}$ alkyl, $C_{3-6}$ alkenyl, aryl $C_{1-6}$ alkyl, hydroxy $C_{2-6}$ alkyl or $C_{1-6}$ alkoxy-$C_{2-6}$ alkyl; and $R_4$ represents hydrogen, $C_{1-6}$ alkyl, $C_{3-6}$ alkenyl, aryl $C_{1-6}$ alkyl; acyloxy $C_{1-6}$ alkyl wherein the acyl portion is aroyl, aryl $C_{2-7}$ alkanoyl or $C_{1-6}$ alkanoyl; $C_{1-6}$ alkylthio $C_{1-6}$ alkyl, arylthio $C_{1-6}$ alkyl; aryloxy $C_{1-6}$ alkyl, aryl $C_{1-6}$ alkyloxy $C_{1-6}$ alkyl; or the group $(CH_2)_qR_6$ where q is zero, 1, 2, 3, 4, 5 or 6 and the alkylene chain $(CH_2)_q$ may be straight or branched; and $R_6$ ia hydroxy, $C_{1-6}$ alkoxy, nitro, cyano; heteroaryl; or $CH_2NHC(=A)NHR_7$ where A is NCN, $NSO_2$ methyl, $NSO_2$ phenyl or $CHNO_2$, and $R_7$ is alkyl;

or $R_6$ is the group $NR_8R_9$ where $R_8$ is hydrogen or $C_{1-6}$ alkyl; and $R_9$ is hydrogen, $C_{1-6}$ alkyl, $C_{3-6}$ alkenyl, aryl; aryl $C_{1-6}$ alkyl or heteroaralkyl, or $R_9$ is the group $SO_2R_{10}$ where $R_{10}$ is $C_{1-6}$ alkyl or aryl; or $R_9$ is the group $COR_{11}$ where $R_{11}$ is hydrogen, $C_{1-6}$ alkyl, aryl; ar $C_{1-6}$ alkyl; $C_{1-6}$ alkoxy, halomethyl, heteroaryl; heteroaralkyl or the group $NHR_{12}$ where $R_{12}$ is hydrogen, $C_{1-6}$ alkyl, $C_{3-8}$ cycloalkyl, aryl; or aryl $C_{1-6}$ alkyl; or $R_8$ and $R_9$ together represents the group $=CR_{13}R_{14}$ where $R_{13}$ represents aryl; or heteroaryl, and $R_{14}$ represents hydrogen or $C_{1-6}$ alkyl;

or $R_6$ is the group $SO_2R_{15}$ in which $R_{15}$ is hydroxy, $C_{1-6}$ alkyl, aryl; or the group $NR_{16}R_{17}$ where $R_{16}$ and $R_{17}$ which may be the same or different, each represent hydrogen or $C_{1-6}$ alkyl;

or $R_6$ is the group $COR_{18}$ where $R_{18}$ is hydrogen, hydroxy, $C_{1-6}$ alkoxy, aryloxy, aryl $C_{1-6}$ alkoxy; $C_{1-6}$ alkyl, aryl, or aryl $C_{1-6}$ alkyl;

or the group $NR_{19}R_{20}$ where $R_{19}$ is hydrogen or alkyl optionally substituted by a hydroxy or $C_{1-6}$ alkoxy group; and $R_{20}$ is hydrogen, $C_{1-6}$ alkyl (optionally substituted by a hydroxy or $C_{1-6}$ alkoxy group), $C_{3-6}$ alkenyl, aryl, aryl $C_{1-6}$ alkyl; or $C_{3-8}$ cycloalkyl; or $NR_{19}R_{20}$ form a pyrrolidino, piperidino, hexamethylenimino, heptamethylenimino, tetrahydropyridino, 4-hydroxypiperidino, 4-$C_{1-3}$ alkylpiperidino, morpholino, 2,6-di-$C_{1-3}$ alkylmorpholino or a thiamorpholino group;

or $R_6$ is the group $CR_{21}=NR_{22}$ where $R_{21}$ is hydrogen, $C_{1-6}$ alkyl, aryl or aryl $C_{1-6}$ alkyl, and $R_{22}$ is hydroxy, $C_{1-6}$ alkoxy, aryl $C_{1-6}$ alkoxy or $-NHC(=B)NH_2$ where B is oxygen or sulphur;

with the proviso that when the group $R_6$ contains a carbon atom through which it is linked to the alkylene group $(CH_2)_q$ then the total number of carbon atoms in the resulting chain is not greater than 6 (i.e., q is not greater than 5);

or $R_3$ and $R_4$ together represent the group $\text{-(-CH=CH-)}_2$ or $\text{-(-CH}_2\text{-)}_4$; and wherein the term aryl as a group or part of a group means phenyl or phenyl substituted by one or more $C_{1-3}$ alkyl or alkoxy groups or halogen atoms; the term heteroaryl as a group or part of a group unless otherwise stated means thienyl, pyridyl, furyl or thiazolyl; the heteroaryl ring may be unsubstituted or substituted by $C_{1-3}$ alkyl, $C_{1-3}$ alkoxy, hydroxy, hydroxy $C_{1-6}$ alkyl, amino $C_{1-6}$ alkyl, $C_{1-6}$ alkylamino $C_{1-6}$ alkyl, di-$C_{1-6}$ alkylamino $C_{1-6}$ alkyl or halogen; the alkyl portion of a heteroalkyl group is a straight or branched $C_{1-4}$ alkyl chain, and the heteroaryl ring is linked to the alkyl portion through either a carbon or nitrogen atom.

2. A compound as claimed in claim 1, in which the groups $R_1$ to $R_4$ have the following meanings:

$R_1$: alkyl containing up to 14 carbon atoms, $C_{5-7}$ cycloalkyl, $C_{3-6}$ alkenyl, aryl $C_{1-6}$ alkyl; $C_{1-4}$ alkyl substituted by a trifluoromethyl group, hydroxy $C_{2-4}$ alkyl, $C_{1-3}$ alkoxy $C_{2-4}$ alkyl, di-$C_{1-3}$ alkylamino $C_{2-4}$ alkyl or heteroaralkyl wherein the heterocyclic portion is furyl, thienyl, pyrrolyl, pyridinyl, pyrimidinyl, triazinyl, oxazolyl, triazolyl or thiazolyl and the alkyl portion is a straight or branched $C_{1-4}$ alkyl chain, and the heteroaryl ring is linked to the alkyl portion through either a carbon or nitrogen atom;

$R_2$: hydrogen, methyl or ethyl; or $R_1R_2N$: pyrrolidino, piperidino, hexamethylenimino, hpetamethylenimino, tetrahydropyridino, 4-hydroxypiperidino, 4-$C_{1-3}$ alkylpiperidino, morpholino, 2,6-di-$C_{1-3}$ alkylmorpholino or thiamorpholino group;

$R_3$: $C_{1-4}$ alkyl or hydroxy $C_{2-4}$ alkyl;

$R_4$: hydrogen, hydroxy, $C_{1-4}$ alkyl, hydroxy $C_{1-4}$ alkyl, $C_{1-3}$ alkoxy $C_{1-4}$ alkyl, phenyl $C_{1-3}$ alkyl, $C_{2-4}$ alkanoyloxy $C_{1-4}$ alkyl, amino $C_{1-4}$ alkyl, $C_{1-3}$ alkylthio $C_{1-4}$ alkyl, amino, $C_{1-4}$ alkylamino, di-$C_{1-4}$ alkylamino, phenyl $C_{1-3}$ alkylamino, or a heteroaryl $C_{1-3}$ alkylamino group where the heteroaryl group is a pyridyl group; or $R_4$ represents the group $N=CHR_{13}$ where $R_{13}$ is a phenyl or pyridinyl group; or $R_4$ represents $(CH)_qR_6$ where q is zero, 1, 2 or 3; and $R_6$ is nitro, cyano, pyridyl or thienyl, $-CH_2NHC(=A)NHR_7$ where A is NCN or $CHNO_2$ and $R_7$ is $C_{1-3}$ alkyl; or the group $SO_2R_{15}$ where $R_{15}$ is hydroxy, $C_{1-3}$ alkyl or aryl; or the group $COR_{18}$ where $R_{18}$ is hydrogen, hydroxy, $C_{1-3}$ alkoxy, $C_{1-3}$ alkyl or the group $NR_{19}R_{20}$ where $R_{19}$ and/or $R_{20}$ are hydrogen or $C_{1-3}$ alkyl or $NR_{19}R_{20}$ form a pyrrolidino, piperidino, hexamethylenimino, heptamethylenimino, tetrahydropyridino, 4-hydroxypiperidino, 4-$C_{1-3}$ alkylpiperidino, morpholino, di-$C_{1-3}$ alkylmorpholino or a thiamorpholino group; or the group $CH=NR_{22}$ where $R_{22}$ is hydroxy or $C_{1-3}$ alkoxy; $R_6$ is the group $NHR_9$ where $R_9$ is the group $SO_2R_{10}$ where $R_{10}$ represents $C_{1-3}$ alkyl, or phenyl optionally substituted by a $C_{1-3}$ alkyl or $C_{1-3}$ alkoxy group; or $R_9$ represents $COR_{11}$ where $R_{11}$ represents hydrogen, $C_{1-3}$ alkyl, $C_{1-3}$ alkoxy, halomethyl, phenyl $C_{1-3}$ alkyl, furyl, pyridyl, thiazolyl, thienyl, phenyl, substituted phenyl with at least one $C_{1-3}$ alkyl or $C_{1-3}$ alkoxy groups, or $NHR_{12}$ where $R_{12}$ is $C_{1-3}$ alkyl, $C_{5-7}$ cycloalkyl, or phenyl or phenyl substituted by a $C_{1-3}$ alkyl or $C_{1-3}$ alkoxy group; or $R_3$ and $R_4$ together represent $+CH=CH+_2$ or $+CH_2+_4$; wherein the term aryl as a group or part of a group means phenyl or phenyl substituted by one or more $C_{1-3}$ alkyl or alkoxy groups or halogen atoms.

3. A compound as claimed in claim 1 in which $R_1$ to $R_4$ have the following meanings:

$R_1$: $C_{1-7}$ alkyl, $C_{1-4}$ alkyl substituted by trifluoromethyl, $C_{2-4}$ alkyl substituted by hydroxy or di-$C_{1-3}$ alkylamino, $C_{5-7}$ cycloalkyl, $C_{3-6}$ alkenyl, phenyl $C_{1-3}$ alkyl or heteroaryl $C_{1-3}$ alkyl wherein the hetero ring is furyl or thienyl and the hetero ring is linked to the alkyl portion through a carbon or nitrogen atom;

$R_2$: hydrogen or methyl; or $R_1R_2N$: represents piperidino, pyrrolidino, hexamethylenimino, tetrahydropyridino or 4-methylpiperidino;

$R_3$: methyl, ethyl or 2-hydroxyethyl;

$R_4$: hydrogen, $C_{1-4}$ alkyl, nitro, $C_{1-3}$ alkylthiomethyl, $C_{1-3}$ alkoxy, $C_{1-4}$ alkyl, $C_{2-4}$ alkanoyloxy $C_{1-4}$ alkyl, phenyl $C_{1-3}$ alkyl, pyridinylmethyl, or the group $N=CHR_{13}$ where $R_{13}$ is phenyl or pyridyl, or the group $(CH_2)_qR_6$ where q is zero, 1, 2 or 3 and $R_6$ is hydroxy, cyano, $CH_2NHC(=A)NHR_7$ (where A is NCN or $CHNO_2$ and $R_7$ is $C_{1-3}$ alkyl); or $R_6$ represents the group $NHR_9$ where $R_9$ is hydrogen, $SO_2R_{10}$ where $R_{10}$ is $C_{1-3}$ alkyl, or $COR_{11}$ where $R_{11}$ is hydrogen, $C_{1-3}$ alkyl, $C_{1-3}$ alkoxy, benzyl, phenyl or $NHR_{12}$ (where $R_{12}$ is phenyl); or $R_6$ represents the group $SO_2R_{15}$ where $R_{15}$ is $C_{1-3}$ alkyl or phenyl or phenyl substituted with one or more $C_{1-3}$ alkyl or alkoxy groups or halogen atoms; or $R_6$ represents the group $COR_{18}$ where $R_{18}$ is hydrogen, hydroxy, or $NR_{19}R_{20}$ where $R_{19}$ and/or $R_{20}$ are hydrogen or $C_{1-3}$ alkyl, or $NR_{19}R_{20}$ forms a piperidino or pyrrolidino group; or $R_6$ represents $-CH=NOH$; or $R_3$ and $R_4$ together represent $+CH=CH+_2$ or $+CH_2+_4$.

4. A compound as claimed in claim 1, in which:

$R_4$: represents hydrogen, $C_{1-6}$ alkyl, $C_{3-6}$ alkenyl, ar $C_{1-6}$ alkyl, acyloxy $C_{1-6}$ alkyl wherein the acyl portion is aroyl, aryl $C_{2-7}$ alkanoyl or $C_{1-6}$ alkanoyl; aryloxy $C_{1-6}$ alkyl; ar $C_{1-6}$ alkoxy $C_{1-6}$ alkyl; or the group $(CH_2)_qR_6$ where $R_6$ represents hydroxy or $C_{1-6}$ alkoxy, or $R_6$ is $NR_8R_9$ where $R_9$ represents hydrogen or $C_{1-6}$ alkyl; or when q is zero, $R_6$: represents $NR_8R_9$ where $R_9$ is $C_{3-6}$ alkenyl, ar $C_{1-6}$ alkyl or heteroaralkyl wherein the heterocyclic portion is thienyl, pyridyl, furyl, or thiazolyl, which group may be unsubstituted or substituted by $C_{1-3}$ alkyl, $C_{1-3}$ alkoxy, hydroxy, hydroxy $C_{1-6}$ alkyl, amino $C_{1-6}$ alkyl, $C_{1-6}$ alkylamino $C_{1-6}$ alkyl, di-$C_{1-6}$ alkylamino $C_{1-6}$ alkyl or halogen; and the alkyl portion is a $C_{1-4}$ straight or branched alkyl chain and the heteroaryl ring is linked to the alkyl portion through either a carbon or nitrogen atom, or $R_9$ is the group $SO_2R_{10}$ or the group $COR_{11}$ (where $R_{11}$ is other than halomethyl); or $R_8$ and $R_9$ together represent $=CR_{13}R_{14}$; wherein the term aryl as a group or part of a group means phenyl or phenyl substituted by one or more $C_{1-3}$ alkyl or alkoxy groups or halogen atoms.

5. A compound as claimed in claim 1 in which $R_1$ to $R_4$ have the following meanings:

$R_1$: $C_{1-7}$ alkyl, $C_{1-4}$ alkyl substituted by trifluoromethyl, $C_{2-4}$ alkyl substituted by hydroxy or di-$C_{1-3}$ alkylamino, $C_{5-7}$ cycloalkyl, $C_{3-6}$ alkenyl, phenyl $C_{1-3}$ alkyl or heteroaryl $C_{1-3}$ alkyl wherein the hetero ring is furyl or thienyl and the hetero ring is linked to the alkyl portion through a carbon or nitrogen atom;

$R_2$: hydrogen or methyl; or $R_1R_2N$: represents piperidino, pyrrolidino, hexamethylenimino, tetrahydropyridino or 4-methylpiperidino;

$R_3$: methyl, ethyl or 2-hydroxyethyl;

$R_4$: hydrogen, $C_{1-4}$ alkyl, nitro, $C_{1-3}$ alkylthiomethyl, $C_{1-3}$ alkoxy, $C_{1-4}$ alkyl, $C_{2-4}$ alkanoyloxy $C_{1-4}$ alkyl, phenyl $C_{1-3}$ alkyl, pyridinylmethyl, or the group $N=CHR_{13}$ where $R_{13}$ is phenyl or pyridyl, or the group $(CH_2)_qR_6$ where q is zero, 1, 2 or 3 and $R_6$ is hydroxy, cyano, $CH_2NHC(=A)NHR_7$ (where A is NCN or $CHNO_2$ and $R_7$ is $C_{1-3}$ alkyl); or $R_6$ represents the group $NHR_9$ where $R_9$ is hydrogen, $SO_2R_{10}$ where $R_{10}$ is $C_{1-3}$ alkyl, or $COR_{11}$ where $R_{11}$ is hydrogen, $C_{1-3}$ alkyl, $C_{1-3}$ alkoxy, benzyl, phenyl or $NHR_{12}$ (where $R_{12}$ is phenyl); or $R_6$ represents the group $SO_2R_{15}$ where $R_{15}$ is $C_{1-3}$ alkyl or phenyl or phenyl substituted with one or more $C_{1-3}$ alkyl or alkoxy groups or halogen atoms; or $R_6$ represents the group $COR_{18}$ where $R_{18}$ is hydrogen, hydroxy, or $NR_{19}R_{20}$ where $R_{19}$ and/or $R_{20}$ are hydrogen or $C_{1-3}$ alkyl, or $NR_{19}R_{20}$ forms a piperidino or pyrrolidino group; or $R_6$ represents —CH=NOH; or R₃ and R₄ together represent ₋(CH=CH)₋₂ or ₋(CH₂)₋₄; and in which Alk represents methylene; Q represents a furan or thiophene ring, optionally substituted by a further substituent R₅ where R₅ is C₁₋₄ alkyl, in which case X represents a bond and either Y is —S— or —CH₂—, n is 1 and m is 2 or Y is —O—, n is 1 and m is 3; or Q represents benzene in which case X represents a bond, Y is —O—, n is zero and m is 3, 4 or 5, or X and Y both represent —O— and n and m are both 2.

6. A compound as claimed in claim 1, in which Alk represents methylene: Q represents a furan or thiophene ring, optionally substituted by a further substituent R₅ where R₅ is C₁₋₄ alkyl, in which case X represents a bond and either Y is —S— or —CH₂—, n is 1 and m is 2 or Y is —O—, n is 1 and m is 3; or Q represents benzene in which case X represents a bond, Y is —O—, n is zero and m is 3, 4 or 5, or X and Y both represent —O— and n and m are both 2.

7. A compound as claimed in claim 1, in which Q is a benzene ring which is incorporated into the rest of the molecule through bonds at the 1- and 3-positions, Y is —O—, n is zero and m is 3 or 4.

8. A compound as claimed in claim 1, corresponding to formula (II)

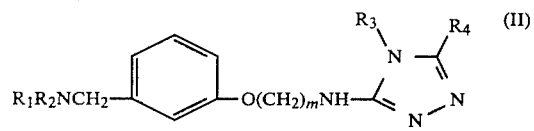

where R₁ and R₂ are methyl groups or together with the nitrogen atom to which they are attached form a pyrrolidino, piperidino or hexamethylenimino group; m is 3 or 4, R₃ is methyl; and R₄ is hydrogen, C₁₋₄ alkyl, C₂₋₄ alkanoyloxy C₁₋₆ alkyl, C₁₋₃ alkylthiomethyl, cyano C₁₋₆ alkyl, or the group $(CH_2)_qR_6$ where q is zero, 1 or 2, and R₆ is hydroxy, $CH_2NHC(=CHNO_2)NHR_7$ (where R₇ is C₁₋₃ alkyl), or the group NHR₉ where R is hydrogen, SO₂R₁₀ (where R₁₀ is C₁₋₃ alkyl) or COR₁₁ (where R₁₁ is C₁₋₃ alkyl), or R₆ is the group SO₂R₁₅ where R₁₅ is C₁₋₃ alkyl, or R₆ is the group COR₁₈ where R₁₈ is hydrogen, hydroxy, or amino; or R₆ is the group CH=NOH; or R₃ and R₄ together represent ₋(CH=CH)₋₂ or ₋((CH₂)₄)₋.

9. A compound as claimed in claim 1, which is:
4-methyl-N-[3-[3-(1-piperidinylmethyl)phenoxy]-propyl]-4H-1,2,4-triazole-3-amine
4-methyl-5-[4-[3-(1-piperidinylmethyl)phenoxy]-butyl]amino-4H-1,2,4-triazole-3-methanol
N-[3-[3-(1-piperidinylmethyl)phenoxy]propyl]-1,2,4-triazolo-[4,3-a]pyridine-3-amine
4-methyl-5-[[3-[3-(1-piperidinylmethyl)phenoxy]-propyl]amino]-4H-1,2,4-triazole-3-acetamide
4-methyl-5-[[3-[3-(1-piperidinylmethyl)phenoxy]-propyl]amino]-4H-1,2,4-triazole-3-methanol
4-methyl-5-(methylsulphonyl)methyl-N-[3-[3-(1-piperidinylmethyl)phenoxy]propyl]-4H-1,2,4-triazole-3-amine and their physiologically acceptable salts.

10. A pharmaceutical composition for the treatment of conditions mediated through H₂-receptors comprising an effective amount of a compound as claimed in claim 1 together with at least one inert pharmaceutically acceptable carrier or diluent, and optionally at least one other active ingredient.

11. A method of treating a condition mediated through histamine H₂-receptors which comprises administering to a patient an effective amount of a compound as defined in claim 1 to relieve said condition.

* * * * *